US010945660B2

(12) United States Patent
Huang et al.

(10) Patent No.: US 10,945,660 B2
(45) Date of Patent: Mar. 16, 2021

(54) NORMALIZED-DISPLACEMENT-DIFFERE-NCE-BASED APPROACH FOR THERMAL LESION SIZE CONTROL

(71) Applicant: KONINKLIJKE PHILIPS N.V., Eindhoven (NL)

(72) Inventors: Sheng-Wen Huang, Ossining, NY (US); Ajay Anand, Fishkill, NY (US); Shriram Sethuraman, Woburn, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1082 days.

(21) Appl. No.: 15/125,598

(22) PCT Filed: Mar. 18, 2015

(86) PCT No.: PCT/EP2015/055597
§ 371 (c)(1),
(2) Date: Sep. 13, 2016

(87) PCT Pub. No.: WO2015/144502
PCT Pub. Date: Oct. 1, 2015

(65) Prior Publication Data
US 2017/0007175 A1    Jan. 12, 2017

Related U.S. Application Data

(60) Provisional application No. 61/970,967, filed on Mar. 27, 2014.

(30) Foreign Application Priority Data

May 9, 2014 (EP) .................................... 14167739

(51) Int. Cl.
*A61B 5/00* (2006.01)
*A61B 8/08* (2006.01)
*A61B 18/12* (2006.01)
*A61B 34/10* (2016.01)
*A61B 8/00* (2006.01)
*G05B 19/042* (2006.01)
*A61B 17/00* (2006.01)
*A61B 18/00* (2006.01)

(52) U.S. Cl.
CPC .............. *A61B 5/4836* (2013.01); *A61B 8/08* (2013.01); *A61B 8/4483* (2013.01); *A61B 8/485* (2013.01);
(Continued)

(58) Field of Classification Search
CPC ......... A61B 5/4836; A61B 8/08; A61B 8/485; A61B 8/4483; A61B 8/5223;
(Continued)

(56) References Cited

U.S. PATENT DOCUMENTS 9,060,670 B1 *   6/2015   Boctor ..................... A61N 7/02
2005/0215899 A1   9/2005   Trahey et al.
(Continued)

FOREIGN PATENT DOCUMENTS

WO    WO-2011161559 A1 *  12/2011  ........... A61B 8/4488

*Primary Examiner* — Keith M Raymond
*Assistant Examiner* — Johnathan Maynard
(74) *Attorney, Agent, or Firm* — Sherry Austin

(57) ABSTRACT

The present invention relates to monitoring biological tissue during a delivery of energy. A probe-driving unit repeatedly drives an integrated push-and-track transducer unit, which is external to the control device, in repeatedly providing at least one ultrasonic push pulse (302) that is suitable for displacing biological tissue at a monitoring location (M), and in providing ultrasonic track pulses (301, 303) suitable for detecting tissue displacement occurring in response to the push pulse at the monitoring location, and in detecting and delivering ultrasonic tissue-response signals (R) relating to the track pulses. An evaluation unit receives the tissue-response signals, determines in real time whether a normalized displacement quantity has reached a threshold value, and provides an output signal when the threshold value has been reached.

19 Claims, 6 Drawing Sheets

(52) U.S. Cl.
CPC .............. *A61B 18/12* (2013.01); *A61B 34/10* (2016.02); *G05B 19/042* (2013.01); *A61B 2017/00106* (2013.01); *A61B 2018/00636* (2013.01); *A61B 2018/00642* (2013.01); *A61B 2018/00666* (2013.01)

(58) Field of Classification Search
CPC ........... A61B 2018/00577; A61B 2018/00642; A61B 2018/00636; A61B 2090/378; A61N 7/02
See application file for complete search history.

(56) References Cited

U.S. PATENT DOCUMENTS

| | | | |
|---|---|---|---|
| 2009/0149753 A1 | 6/2009 | Govari et al. | |
| 2010/0069751 A1* | 3/2010 | Hazard | A61B 5/415 600/438 |
| 2010/0188571 A1 | 7/2010 | Savery et al. | |
| 2010/0256530 A1* | 10/2010 | Varghese | A61B 5/015 600/587 |
| 2010/0286519 A1* | 11/2010 | Lee | A61B 8/08 600/439 |
| 2010/0286520 A1* | 11/2010 | Hazard | G01S 7/52042 600/439 |
| 2010/0317971 A1* | 12/2010 | Fan | G01S 15/8993 600/439 |
| 2011/0251529 A1* | 10/2011 | Petruzzello | A61B 8/08 601/3 |
| 2011/0306881 A1* | 12/2011 | Liu | A61B 8/485 600/439 |
| 2012/0302877 A1 | 11/2012 | Harks et al. | |
| 2013/0096597 A1* | 4/2013 | Anand | A61N 7/00 606/169 |
| 2014/0323862 A1 | 10/2014 | Silverman et al. | |
| 2017/0156705 A1* | 6/2017 | Galluzzo | A61B 90/37 |
| 2018/0271577 A1* | 9/2018 | Bharat | A61B 8/08 |

* cited by examiner

NORMALIZED-DISPLACEMENT-DIFFERENCE-BASED APPROACH FOR THERMAL LESION SIZE CONTROL

FIELD OF THE INVENTION

The present invention relates to a tissue-monitoring device for monitoring biological tissue in a monitoring session during a delivery of energy to the tissue. It further relates to a monitoring method for monitoring biological tissue in a monitoring session during a delivery of energy to the tissue. It also concerns an energy-delivery device for delivering energy to biological tissue. Furthermore, the invention provides a method for delivering energy to biological tissue.

BACKGROUND OF THE INVENTION

WO 2011/161559 A1, also published under US20130096597A1, which is incorporated herein by reference in its entirety, discloses examining an effect of delivering high-intensity focused ultrasound (HIFU) energy to biological tissue to cause a mechanical property of biological tissue to change, as in ablation. An effect of the delivery of HIFU energy is examined in more than one spatial dimension to, for example, make an ablation halting decision for a treatment region or for a location within the region. Halting decisions can be based on lesion-central and/or lesion-peripheral longitudinal displacement of treated tissue evaluated in real time against a characteristic curve. Steering in the azimuthal and/or elevation direction is afforded by, for example, linear, or 2D, multi-channel ultrasound arrays for therapy and imaging. Protocols includable are region-wide scanning and location-by-location completion for both HIFU therapy and tracking acoustic-radiation-forced-based displacement of treated tissue.

SUMMARY OF THE INVENTION

It is an object of the present invention to provide an alternative for monitoring biological tissue during a delivery of energy.

In a first aspect of the present invention a tissue-monitoring device for monitoring biological tissue in a monitoring session during a delivery of energy to the tissue is provided. The tissue-monitoring device comprises:
  a probe-driving unit, which is configured to provide probe-driving signals suitable for driving an integrated push-and-track transducer unit of a measurement probe unit, which is external to the control device, in repeatedly providing at least one ultrasonic push pulse that is suitable for displacing biological tissue at a monitoring location, and in providing ultrasonic track pulses suitable for detecting tissue displacement occurring in response to the push pulse at the monitoring location, and in detecting and delivering ultrasonic tissue-response signals relating to the track pulses;
  an evaluation unit, which is configured to receive the tissue-response signals and to determine in real time
    a current value of a displacement quantity indicative of an amount of tissue displacement detected,
    a current maximum of the displacement quantity since the beginning of the monitoring session, and
    a normalized displacement quantity that depends on a ratio between the current value and the current maximum of the displacement quantity, and
  whether the normalized displacement quantity has reached a threshold value, and to
  provide an output signal when the threshold value has been reached.

The tissue-monitoring device of the first aspect of the present invention controls operation of an external integrated push-and-track ultrasound transducer unit in monitoring tissue displacement at a monitoring location.

The tissue-monitoring device thus provides control for the one and the same ultrasound transducer unit in performing ultrasound push pulses and ultrasound track pulses for the purpose of monitoring tissue during a delivery of energy to the tissue. This forms a new concept of tissue monitoring in comparison with that known from WO 2011/161559A1, where different ultrasound transducer units, one for providing therapy pulses and push pulses, and another for providing track pulses, use separate control and a synchronization between the different transducer units in tissue monitoring sequences comprising push and track pulses. The tissue-monitoring device of the present invention allows achieving a particularly low expenditure for control and synchronization in the delivery of push and track pulses for monitoring biological tissue.

With the present invention, the ultrasound tissue-monitoring device is provided that can be fully independent from a device for energy delivery. While a coupling between the tissue-monitoring device and a given energy-delivery device may be useful in certain application cases, which will be described further below by way of embodiments, this is not a requirement at all. In contrast to WO 2011/161559A1, the present invention enables a complete independence between an energy-delivery device and the tissue-monitoring device without a need of any coupling.

The term "integrated push-and-track transducer unit" is used herein to express that a single ultrasound transducer unit is used to provide the push pulses and the track pulses. The push-and-track transducer unit is external to the tissue-monitoring device, which means that the tissue-monitoring device as such is fully functional without a push-and-track transducer unit. Embodiments incorporating the tissue-monitoring device and a measurement probe unit that includes an integrated push-and-track transducer unit will be described further below in the context of a tissue-monitoring system.

In the following, embodiments of the tissue-monitoring device of the first aspect will be described.

For monitoring the tissue, the evaluation unit determines a quantity indicative of an amount of tissue displacement, which is a suitable quantity for an elastographic tissue-monitoring approach. From this, a normalized displacement quantity is determined. In one embodiment of the tissue-monitoring device, the evaluation unit is configured to determine the normalized displacement quantity as a normalized displacement according to $$ND(t) = \frac{D(t)}{D_{max}(t)},$$

wherein
  t is a time difference with respect to a beginning of the monitoring session,
  ND(t) is the current value of the normalized displacement,
  D(t) is the current value of the displacement quantity,
  $D_{max}(t)$ is the current maximum of the displacement quantity detected during the monitoring session.

The current maximum is the maximum value of the displacement quantity that has been observed up to the time t during a given monitoring session. It will thus change every time a new maximum value has been reached during the given monitoring session.

In another embodiment, the evaluation unit is configured to determine the normalized displacement quantity as a normalized displacement difference according to $$NDD(t)=1-ND(t),$$

wherein NDD(t) is the normalized displacement difference, and to determine from the determined normalized displacement difference an extension of the ablation zone using a calibration function with prestored calibration parameters.

The calibration function preferably defines the extension of the ablation zone with two calibration parameters as a linear function of the normalized displacement difference. In another embodiment, which achieves an even better accuracy, the calibration function defines the extension of the ablation zone three calibration parameters as a quadratic function of the normalized displacement difference. Instead of a functional representation in terms of calibration parameters of a mathematical function, the calibration function can be provided in the form of a set of values assigning an extension of the ablation zone to a given value of NDD(t). Different calibration functions may be provided for different monitoring locations and different parameters of the performed energy delivery, such as type of energy, energy density, or tissue type, type of energy-delivery device, characteristics of the ultrasound beam.

An important application case of the tissue-monitoring device is in the control of the energy delivery. An energy delivery to biological tissue, especially in medical applications, shall not create tissue damage beyond a desired location, which in many cases is a predefined volume, such as a volume containing tissue to be necrosed by the energy delivery. To this end, the monitoring location must be chosen suitably to provide a real-time indication of an achieved extension of the ablation zone that is currently being created by energy delivery.

A determination of a suitable monitoring location is in some embodiments to be made by a manual input by an operator of the tissue-monitoring device. Preferred embodiments additionally or alternative comprise a monitoring-control unit, which is configured to
- receive a control input indicative of a desired spatial extension of a planned tissue ablation zone at a planned location of energy delivery,
- determine, from the control input, the monitoring location at a peripheral location of the planned tissue ablation zone, and to
- determine the threshold value of the normalized displacement quantity in dependence on the determined monitoring location.

These embodiments make use of a determination of the monitoring location in a periphery of the planned tissue ablation zone. The determined monitoring location is maintained throughout the monitoring session. Energy-delivery to biological tissue involves generation of heat at the planned ablation zone which is accompanied by formation of gas bubbles around a core of the ablation zone. This can introduce artefacts in displacement estimation at these locations, making tissue monitoring based on stiffness less reliable. Moreover, in minimally invasive therapy modalities, the therapy device applicator is present in the field of view of the ultrasound image. The presence of metal devices in soft tissue will disturb shear wave induction and propagation, and affect tissue displacement. Strong ultrasound backscatter reflections from the metal in these devices also introduce artefacts in displacement estimation. Based on these observations, the present embodiment avoids placing a monitoring location, for instance an ultrasound imaging plane, at or close to the core of the planned ablation zone. Rather, the monitoring location is selected in the periphery of the planned ablation zone. The term "periphery" is used here to indicate a location that is away from a central or core region of a planned tissue ablation zone. Such a location is thus closer to the edge of the ablation zone than the center or core. As an example, a monitoring location may be chosen at a distance of at least 3, preferably at least 4, and particularly at least 5 mm from the planned position of an energy-delivery probe, such as an ablation needle, which determines a planned core of a tissue ablation zone. Typically, the monitoring location is selected in further dependence on a known beam characteristic of the ultrasound push-and-track transducer. In particular, the monitoring location should be located far enough from an energy-delivery probe to avoid artefacts in backscattered ultrasound signals.

The methodology of the present embodiment allows applying a tissue monitoring system according to any kind of energy delivery to the tissue as it avoids the problems that occur in some environments where the monitoring location has heretofore been chosen near the center of a planned ablation zone or near an instrument.

A suitable monitoring location at a periphery is in one embodiment determined fully automatically based on a control input providing the position and extension of the planned tissue ablation zone. In another embodiment, an automatic determination of the monitoring location at the periphery of the tissue ablation zone can be influenced initially in a desired way by user input, or adjusted by way user input after an initial suggestion by the monitoring-control unit. For instance, the user may provide additional input determining further monitoring parameters, such as spot-, line- or plane-type (2D) monitoring, or by determining an orientation of a line or plane.

In a further embodiment, the monitoring-control unit includes a threshold-providing unit, which is configured receive at its input a desired spatial extension of a planned tissue ablation zone in the tissue, and to determine, using the calibration function, and provide at its output a threshold value of the normalized displacement difference for the given desired spatial extension of the planned tissue ablation zone. This allows automatically determining a condition for triggering an end of an energy-delivery based on a detecting that the planned extension of the tissue ablation zone has been reached. For instance, the threshold values can be expressed as $$NDD_{th}(x)=1-ND_{end}(x),$$

wherein
- x is a quantity indicative of a desired spatial extension of a planned tissue ablation zone in the tissue,
- $NDD_{th}(x)$ is the threshold value for a given desired spatial extension of the planned tissue ablation zone,
- $ND_{end}(x)$ is a value of the normalized displacement at the point of reaching the desired spatial extension x.

The value $NDD_{th}(x)$ can be determined at the time of planning an energy-delivery session without requiring user input, based on a given calibration of the monitoring systems for the energy-delivery device and the monitoring location to be used, and the type of tissue to be treated.

In a further embodiment of the tissue monitoring device the probe-driving unit is configured to drive the measurement probe in providing a first ultrasonic track pulse before providing the push pulse and a second ultrasonic track pulse after providing the ultrasonic push pulse. This form of tracking is particularly suited for determining tissue elasticity or stiffness at a periphery of a planned tissue ablation zone.

Another embodiment forms a tissue monitoring system that comprises the tissue-monitoring device according to the first aspect or one of its embodiments and further comprises a measurement probe unit, which is configured to receive the probe-driving signals and to deliver the tissue-response signal and which comprises an integrated push-and-track transducer unit configured to provide the at least one ultrasonic push pulse and the ultrasonic track pulses, and which is configured to detect the ultrasonic tissue-response signals relating to the track pulses.

An advantage of the tissue-monitoring system of the present embodiment that it provides an independent tissue-monitoring equipment, which can be used in connection with any kind of energy delivery to biological tissue. This flexibility opens a wide field of applications and use cases of the tissue-monitoring device, in both research and clinical therapy. The tissue-monitoring device can be applied for monitoring tissue displacement and thus tissue elasticity properties in different technological environments used for energy delivery, i.e., under exposure of the tissue to any one of a wide range of energy forms, such as exposure RF currents, light exposure, in particular exposure to laser light, direct exposure to heat or extraction of heat, or any other kind of exposure to energy.

The integrated push-and-track transducer unit and thus the measurement-probe unit may be provided in different forms, depending on the desired application case. In some embodiments, the push-and-track transducer unit forms a linear array formed by a plurality of individual ultrasound transducers, or a two-dimensional (2D) matrix of ultrasound transducers, or a phased array of ultrasound transducers. The push-and-track transducer unit provides ultrasound to the tissue and detects back-scattered ultrasound in response to the provided ultrasound. Depending on the particular embodiment, the back-scattered ultrasound can provide image information indicative of a elasticity response within a tissue region at the monitoring location, the tissue region being either essentially zero-dimensional (a spot), one-dimensional (a line), two-dimensional (a plane or a surface of a volume) or three-dimensional (a volume).

In different embodiments the measurement-probe unit is configured to be positioned with respect to a monitoring location by computer control or manually. In other embodiments the measurement-probe unit comprises a push-and-track transducer unit at an end of a shaft to be introduced internally, as by the mouth of a patient under anaesthesia. The probe may contain beam-forming circuitry. However, in other embodiments the beam-forming circuitry is arranged in the probe-driving unit.

Advantageously, the measurement-probe unit comprises only one, i.e., a single measurement probe for the delivery of, the at least one ultrasonic push pulse and the delivery and detection of the ultrasonic track pulses.

According to a second aspect of the present invention, the tissue-monitoring device of the first aspect of the invention or any of its embodiments described herein, including embodiments forming a tissue-monitoring system, is advantageously a part of an energy-delivery device for delivering energy to biological tissue. The energy-delivery device further comprises an energy-delivery unit. The energy-delivery unit comprises an energy-delivery probe, which is configured to deliver energy in an energy amount suitable for necrosing tissue to form a desired tissue ablation zone when positioned at a delivery location. The energy-delivery unit is preferably configured to receive the output signal provided by the tissue-monitoring device and to stop delivering energy upon reception of the output signal.

The energy-delivery device of the second aspect of the present invention shares the advantages of the respective embodiments of the tissue-monitoring device and the tissue-monitoring system. In particular, it provides a separation of the equipment for energy delivery to the tissue from the equipment used for tissue monitoring. This for instance allows providing an equipment family covering different energy-delivery units for different types of energy delivery that each can be combined with one and the same tissue-monitoring system.

According to a third aspect of the present invention, a monitoring method for monitoring biological tissue in a monitoring session during a delivery of energy to the tissue is provided. The method comprises
    providing probe-driving signals suitable for driving an integrated push-and-track transducer unit of a measurement probe unit, which is external to the control device, in repeatedly providing at least one ultrasonic push pulse that is suitable for displacing biological tissue at a monitoring location, and in providing ultrasonic track pulses suitable for detecting tissue displacement occurring in response to the push pulse at the monitoring location, and suitable for detecting and delivering ultrasonic tissue-response signals relating to the track pulses;
    determining from the tissue-response signals in real time
    a current value of the displacement quantity, which is indicative of an amount of tissue displacement detected,
    a current maximum of the displacement quantity since the beginning of the monitoring session,
    a current value of a normalized displacement quantity, which depends on a ratio between the value of the displacement quantity and the current maximum of the displacement quantity, and
    whether the normalized displacement quantity has reached a predetermined threshold value of the normalized displacement quantity, and
    providing an output signal when the predetermined threshold value of the normalized displacement quantity has been reached.

The method of the third aspect of the present invention shares the advantages of the tissue-monitoring device of the first aspect of the invention. Embodiments of this method, as well as their advantages and variants correspond to those described in the context of the other aspects of the present invention.

In the following, further preferred embodiments of the monitoring method of the first aspect of the invention will be described.

One preferred embodiment comprises
    receiving a control input indicative of a desired spatial extension of a planned tissue ablation zone at a planned location of energy delivery,
    determining, from the control input, a monitoring location at a peripheral location of the planned tissue ablation zone, and determining, in dependence on the determined monitoring location, the threshold value of the normalized displacement quantity.

Another embodiment further comprises determining the normalized displacement quantity as a normalized displacement difference according to NDD(t)=1ND(t), wherein $$ND(t) = \frac{D(t)}{D_{max}},$$

t is a time difference with respect to a beginning of the monitoring session,

ND(t) is the current value of the normalized displacement,

D(t) is the current value of the displacement quantity, $D_{max}$ is the current maximum of the displacement quantity detected during the monitoring session, and NDD(t) is the normalized displacement difference, and determining from the determined normalized displacement difference an extension of the ablation zone using a calibration function with prestored calibration parameters.

Preferably, the calibration function defines the extension of the ablation zone with two calibration parameters as a linear function of the normalized displacement difference or with three calibration parameters as a quadratic function of the normalized displacement difference.

The monitoring method is in preferred application scenarios used in the context of a method for delivering energy to biological tissue, which method comprises delivering energy in an energy amount suitable for necrosing tissue to a desired ablation zone of the tissue via an energy-delivery probe positioned at a delivery location;

performing a monitoring session for monitoring the tissue according to the method of the second aspect of the present invention or one of its embodiments described herein, and ending the delivery of energy to the tissue when the output signal has been provided.

A fourth aspect of the present invention is a tissue-monitoring computer program comprising program code means for causing a computer to carry out the monitoring method of the second aspect of the present invention or one of its embodiments when said computer program is executed on a computer.

A fifth aspect of the present invention is an energy-delivery control program comprising program code means for causing a computer to carry out the energy-delivery method of claim 13 or one of its embodiments when said computer program is executed on a computer.

It shall be understood that the tissue monitoring device of claim 1, the energy-delivery device of claim 9, the tissue monitoring method of claim 10, the energy-delivery method of claim 13, the tissue-monitoring computer program of claim 14 and the energy-delivery computer program have similar and/or identical preferred embodiments, in particular, as defined in the dependent claims.

BRIEF DESCRIPTION OF THE DRAWINGS

In the following drawings

DETAILED DESCRIPTION OF EMBODIMENTS

Figure 1:
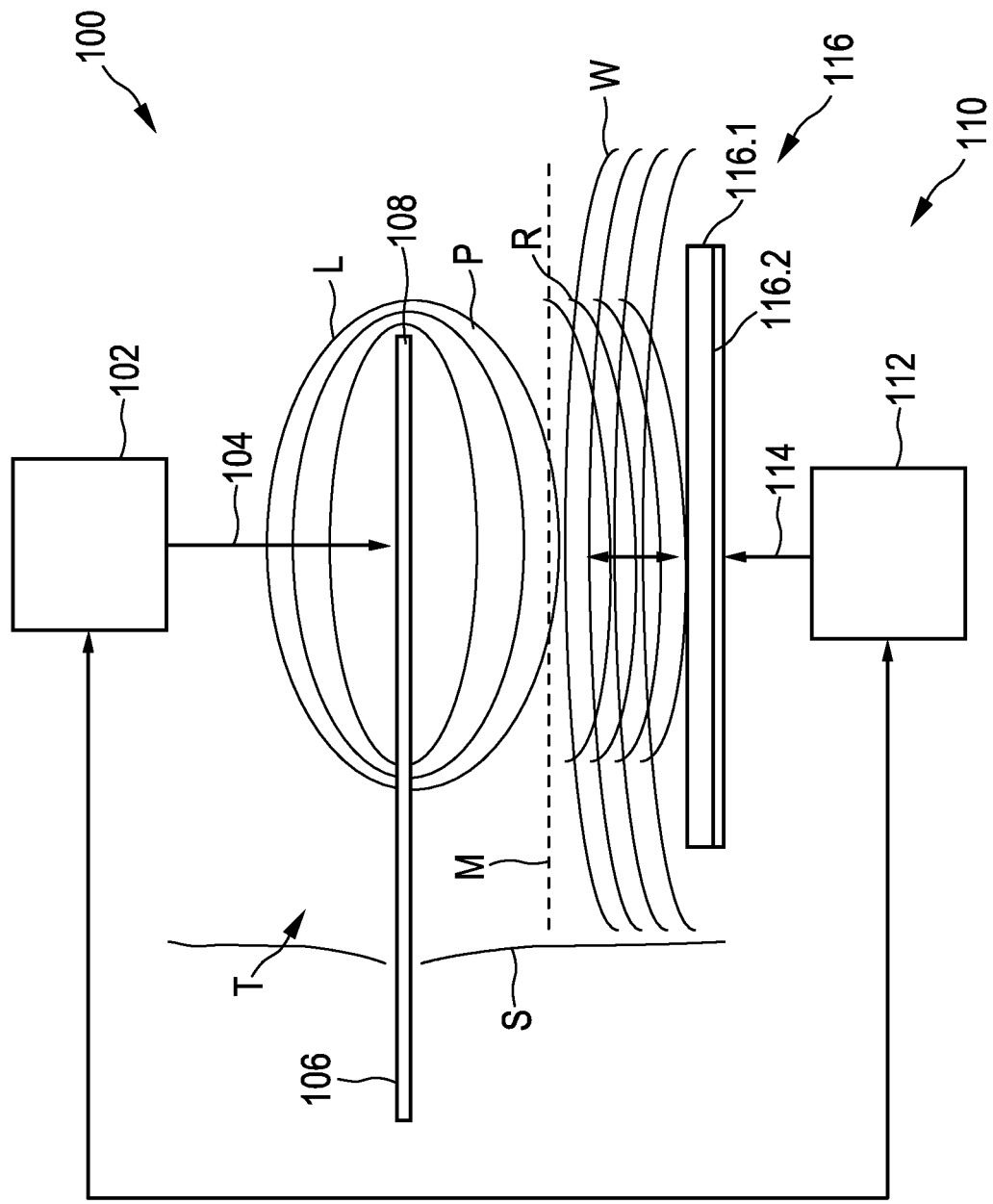
FIG. 1 shows a schematic illustration of an embodiment of an energy-delivery device controlled by a tissue-monitoring device according to an embodiment of the present invention in an exemplary application scenario.

FIG. 1 shows a schematic illustration of an embodiment of an energy-delivery device controlled by a tissue-monitoring device according to an embodiment of the present invention in an exemplary application scenario.

Energy-delivery devices implementing a thermal ablation technique provide an advantageous way of treatment of biological tissue. This holds in particular in medical applications because these techniques allow application of minimal invasive techniques, requiring for instance only needles for energy delivery to the tissue. Example forms of energy that can be delivered this way are alternating electric currents (AC), in particular in a radio frequency (RF) range, electromagnetic waves, such as microwaves, non-invasive heat sources, such as high-intensity focused ultrasound (HIFU). In most of the mentioned procedures, the tissue to be treated by the respective form of energy delivery is heated to above 60° C. and coagulated, resulting in tissue ablation.

In the following, an exemplary embodiment of an energy-delivery device 100 shown in FIG. 1 will be described. The energy-delivery device 100 has an energy-delivery unit 102, which is connected with an energy-delivery probe 106. The connection is represented by an arrow 104, which represents only the functional aspect of the connection and is not intended to represent how the connection is actually established. This depends on the particular technique used and is per se known to a person of ordinary skill in the art. The energy-delivery probe 106 is in the present form a needle inserted into a biological tissue T, which in FIG. 1 is assumed to extend to the right of a line S representing a surface of the biological tissue. The energy-delivery probe 106 is configured to deliver energy in an energy amount suitable for necrosing the tissue T in a desired ablation zone of the tissue when positioned at a delivery location, which in FIG. 1 is represented by the given position of an electrode 108 of the energy-delivery probe 106.

Thus, the exemplary energy-delivery device 100 is configured to delivery of energy in the form of radio frequency electromagnetic energy to effect RF ablation (RFA). The electrode 108 of the energy-delivery probe 106 is an active electrode through which an alternating current is conducted, typically at a frequency in the radio frequency range, such as 460-500 kHz. The current propagates through the tissue T to grounding pads (not shown). In medical applications, such grounding pads may be placed either on the back or the thigh of a patient. The current causes ionic agitation and frictional heating. Heat is then dissipated through thermal conduction to ablate tissue in the desired tissue ablation zone L, thus forming a lesion. In medical applications, this technique may be used to treat a tumor, or malfunctions of the human heart.

The ablation zone L typically covers a three-dimensional volume. Known treatment protocols use a simplistic prediction of an extension of the tissue ablation zone L in the form of an assumed spherical/elliptical ablation volume. Such predictions are typically provided by a device specification for the energy-delivery device. It has been observed that actual treatment volumes greatly deviate from predictions of this kind, resulting in large recurrence rates of approximately 35%.

One common reason for the high recurrence rates is the inability to precisely monitor and control ablation size. Real-time feedback to a user of the energy-delivery device, such as a clinician performing surgery with the energy-delivery device, can currently be achieved with reasonable accuracy with magnetic-resonance-based temperature imaging. However, MRI is expensive and often times not readily available. RFA may be performed under ultrasound or computer tomography (CT) guidance.

The present embodiment uses ultrasound for monitoring the tissue. Ultrasound is a modality that is commonly used for image guidance during placement of the needle 106. Due to its ease of use and availability it is a preferred method for monitoring the formation of lesions in the biologic tissue.

A tissue-monitoring system 110 shown in FIG. 1 includes a tissue-monitoring device 112, which has a probe-driving unit and an evaluation unit, as will be described in more detail with reference to the embodiment of FIG. 2 further below. It further includes a measurement probe unit 116, which receives energy and control information from the tissue-monitoring device 112 through a suitable connection 114. The measurement probe unit 116 and the tissue-monitoring device 112 are different individual devices. In the present embodiment, the measurement probe unit 116 incorporates an integrated push-and-track transducer unit 116.1 for delivering ultrasound energy W for monitoring a desired monitoring location M, which in the present example suitably is a plane indicated by a dashed line in FIG. 1. In the present embodiment, the push-and-track transducer unit 116.1 comprises a two-dimensional array transducers suitable for imaging and monitoring tissue elasticity in the desired plane forming the monitoring location M. Further components of the measurement probe 116, including circuitry for providing driving signals generated by a probe-driving unit of the tissue-monitoring device 112 to the different individual transducers of the push-and-track transducer unit 116.1 and for delivering detected response signals back to an evaluation unit of the tissue-monitoring device 112 are summarized under the reference label 116.2. The tissue-monitoring device 112 therefore not only controls the delivery of ultrasound W by the integrated push-and-track transducer unit 116.1 via the push and track pulses, but also the reception of a response by the measurement probe 116 from the monitoring location M in the form of ultrasound R scattered back from tissue in or near the monitoring location M. In particular, thus, according to the present embodiment, the same push-and-track transducer unit 116.1 is used to apply ultrasound radiation force pulses and ultrasound track pulses for quantifying a tissue displacement. This will be described in more detail further below with reference to FIGS. 2 to 6.

The tissue monitoring location M is determined before the beginning of an energy-delivery treatment and a corresponding monitoring session. In particular, according to the present embodiment, the monitoring location M is determined to be located in a periphery P of the planned ablation zone L. More specifically, the monitoring location M is in a region that is not subject to a formation of gas bubbles and at a suitable distance from the energy-delivery probe 106 so as to avoid artefacts in the ultrasound response of the monitored tissue ablation zone. In known RFA or microwave ablation technologies, the presence of gas bubbles or metal in the monitored region is a source of perturbations obscuring the response signals. By selecting the monitoring location M in the periphery P of the planned tissue-ablation zone L, the ultrasound displacement monitoring can be performed even in the presence of foreign objects such as a metallic electrode 108 that is to be arranged in the core region of the planned tissue ablation zone L.

Figure 2:
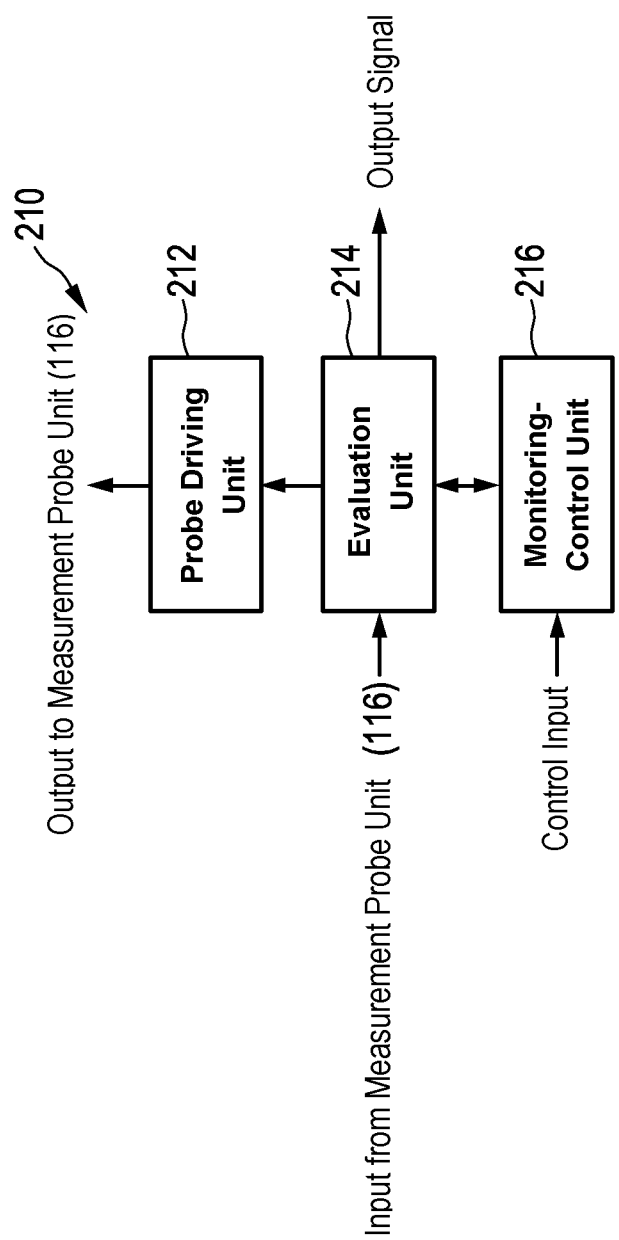
FIG. 2 shows a block diagram of another embodiment of a tissue-monitoring device.
Figure 3:
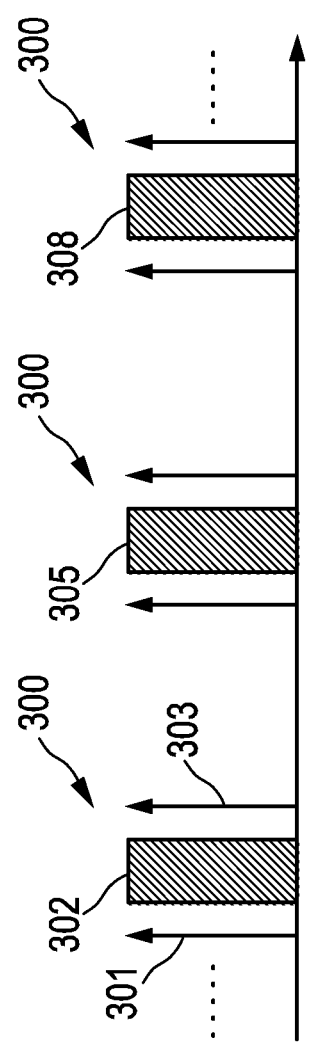
FIG. 3 shows a schematic illustration of a pulse sequence used in an embodiment of a tissue-monitoring device and of a tissue-monitoring method.

Additional reference is now made to FIGS. 2 and 3 in parallel. FIG. 2 shows a block diagram of an embodiment of a tissue-monitoring device 210 that can be used in the application situation of FIG. 1 as the tissue-monitoring device 110. FIG. 3 shows a schematic illustration of an ultrasound pulse sequence generated by the tissue-monitoring device 210. The tissue monitoring device 210 has a probe-driving unit 212. The probe-driving unit 212 is configured to repeatedly drive a measurement probe, such as the measurement probe unit 116 with the integrated push-and-track transducer unit 116.1, in providing an ultrasonic measurement sequence 300, in particular comprising at least one ultrasonic push pulse 302 that is suitable for displacing the tissue T at the monitoring location M at least two ultrasonic track pulses 301, 303 suitable for detecting tissue displacement occurring in response to the push pulse 302 at the monitoring location M. Further measurement sequences are shown in FIG. 3 around subsequent push pulses 305, 308. The determination of tissue displacement is thus enabled by detecting ultrasound scattered from the tissue in the monitoring location M in response to the track pulses 301, 303, which are provided shortly before (301) and shortly after (303) the push pulse 302. The push pulse 302 thus forms a push pulse, and the two short track pulses 301, 303 are transmitted to acquire ultrasound pulse-echo data, one before and the other after the long push pulse used to provide acoustic radiation force and induce displacement.

By comparing speckle patterns corresponding to scattered short pulses using speckle tracking, tissue displacement due to the push pulse can be measured. In the course of treatment, this measurement sequence 300 is repeated, as indicated in FIG. 3. The tissue-monitoring device 210 further comprises an evaluation unit 214, which is configured to receive the tissue-response signals and to determine in real time the following:

a) a current value of a displacement quantity indicative of an amount of tissue displacement detected. Preferentially, the normalized displacement quantity is a normalized displacement according to $$ND(t) = \frac{D(t)}{D_{max}},$$

wherein t is a time difference with respect to a beginning of the monitoring session, ND(t) is the current value of the normalized displacement, D(t) is the current value of the displacement quantity, $D_{max}$ is the current maximum of the displacement quantity detected during the monitoring session.

b) the current maximum of the displacement quantity since the beginning of the monitoring session. One way to maintain and finally determine the overall maximum of the displacement quantity during a monitoring session in real time will be described in more detail in the context of FIG. 6.

c) a normalized displacement quantity that depends on a ratio between the current value and the current maximum of the displacement quantity. In particular, the normalized displacement difference may be determined according to $$NDD(t)=1-ND(t)$$

The evaluation unit is further configured to determine whether the normalized displacement quantity has reached a threshold value, and to provide an output signal when the threshold value has been reached.

The tissue-monitoring device 210 further comprises a monitoring-control unit 216, which is configured to
- receive a control input indicative of a desired spatial extension of a planned tissue ablation zone at a planned location of energy delivery,
- determine, from the control input, the monitoring location at a peripheral location of the tissue ablation zone, and to
- determine the threshold value of the normalized displacement quantity in dependence on the control input and on the determined monitoring location.

Other embodiments alternatively or additionally provide manual control options for the user in order to determine or at least influence the monitoring location.

Figure 4:
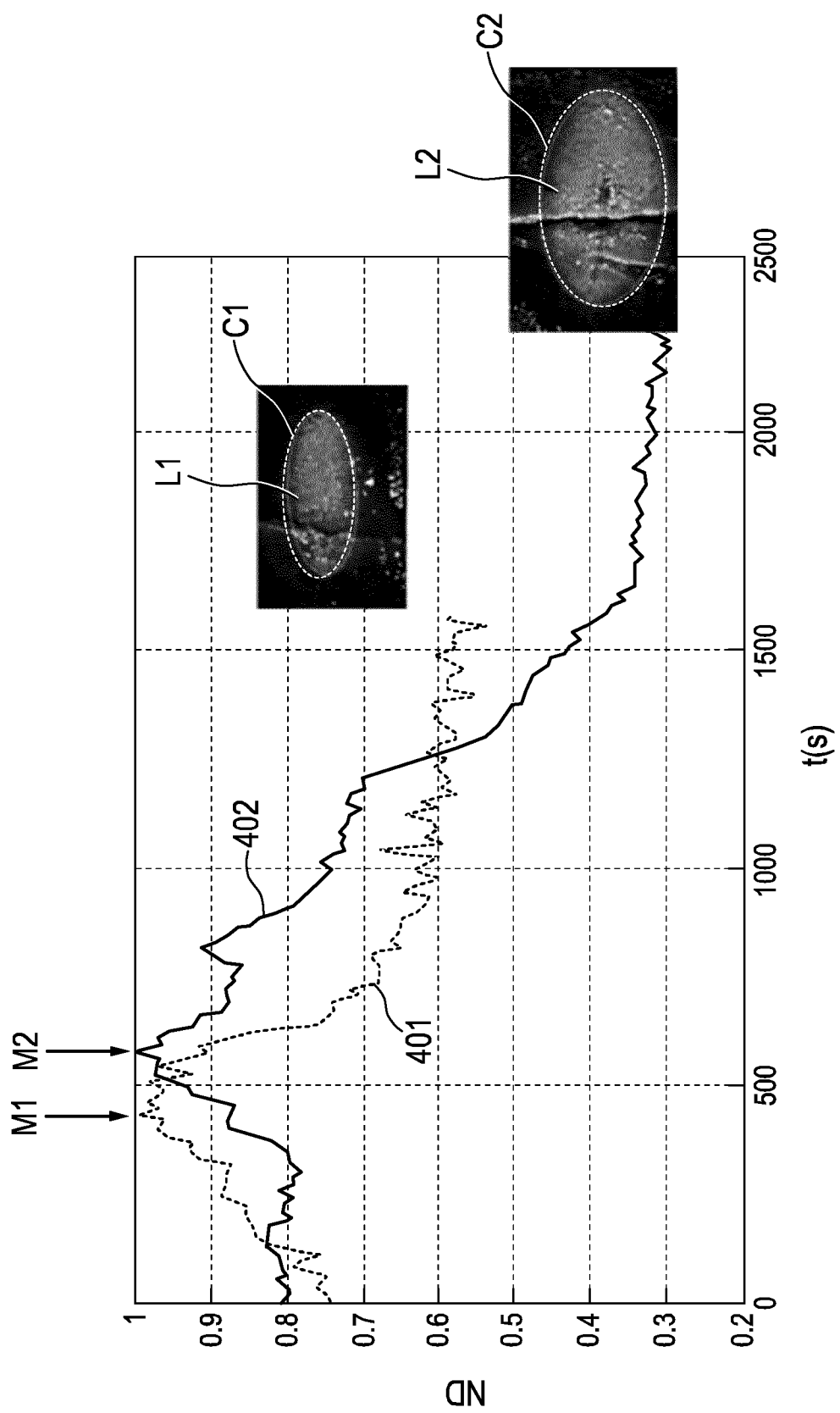
FIG. 4 shows a diagram with two traces and of a normalized displacement ND(t) plotted as a function of energy-delivery time (t) in seconds, and embedded images of corresponding lesions and due to the respective energy delivery.

FIG. 4 is a diagram showing two traces 401 and 402 of a normalized displacement ND(t) as a function of treatment time (t) in seconds, and embedded images of the corresponding lesions L1 and L2 due to the respective treatment by energy delivery. RFA experiments on excised bovine livers as sample biological tissue were conducted to demonstrate the feasibility of deciding the end point of treatment to achieve the desired lesion size based on a detected change of a normalized tissue displacement difference, the tissue displacement being induced by acoustic radiation force.

The pulse sequence was designed to allow for tracking displacement along the push direction. The push duration of the push pulses lasted 0.8 ms and a tracking pulse was fired 1.45 ms after the push pulse ends. The monitoring location M in the RFA experiments corresponds to an ultrasound monitoring plane and was placed at 5 mm from the probe/tine. Data collection was started slightly earlier than the onset of treatment and continued beyond the end point of treatment. Every 15 seconds one measurement was performed. Displacement was estimated at a depth slightly shallower than the tine depth to avoid interference from the tine picked up by elevational sidelobes of the probe.

The two traces 401 and 402 and images of lesions L1, L2 were obtained by two different energy-delivery sessions in different locations of the sample biological tissue. The energy delivery was performed using a radio frequency ablation (RFA) technique. Displacement amounts detected by ultrasonic monitoring in accordance with a monitoring method described in the context of FIG. 3 were normalized with respect to corresponding displacement maxima, i.e., peak displacement amount during a session. The positions of the maxima are labeled M1 and M2, respectively. Also shown are images of created ablation zones (lesions) L1 and L2. The images were recorded after ending the RFA treatment. Dashed white circles C1 and C2 in the images indicate the spatial extension of the created ablation zone at an end point of the RFA treatment. It was observed that after stopping the RFA treatment, tissue continued to stiffen, but at a slower rate. Treatment of spot 1 (trace 401, lesion L1) was stopped when tissue stiffening was less prominent compared to treatment of spot 2 (trace 402, lesion 2). The normalized displacement difference NDD at the end point of treatment (indicated by the dashed white circles) is determined according to the formula $(1-ND_{end})$, where $ND_{end}$ is the normalized displacement relative to the peak displacement at the end point of treatment. The NDD values, at which the energy delivery was terminated, are 0.26 and 0.66 for lesions L1 and L2, respectively.

The images of the lesions L1 and L2 are provided with a scaling of the lateral extension. The scale is the same for both images. As the photos show, lesion 1 is much smaller than lesion 2, implying correlation between NDD and lesion size.

A total of ten lesions were created by RFA with two lesions per bovine liver to establish relationship between lesion diameter/width and NDD.

Figure 5:
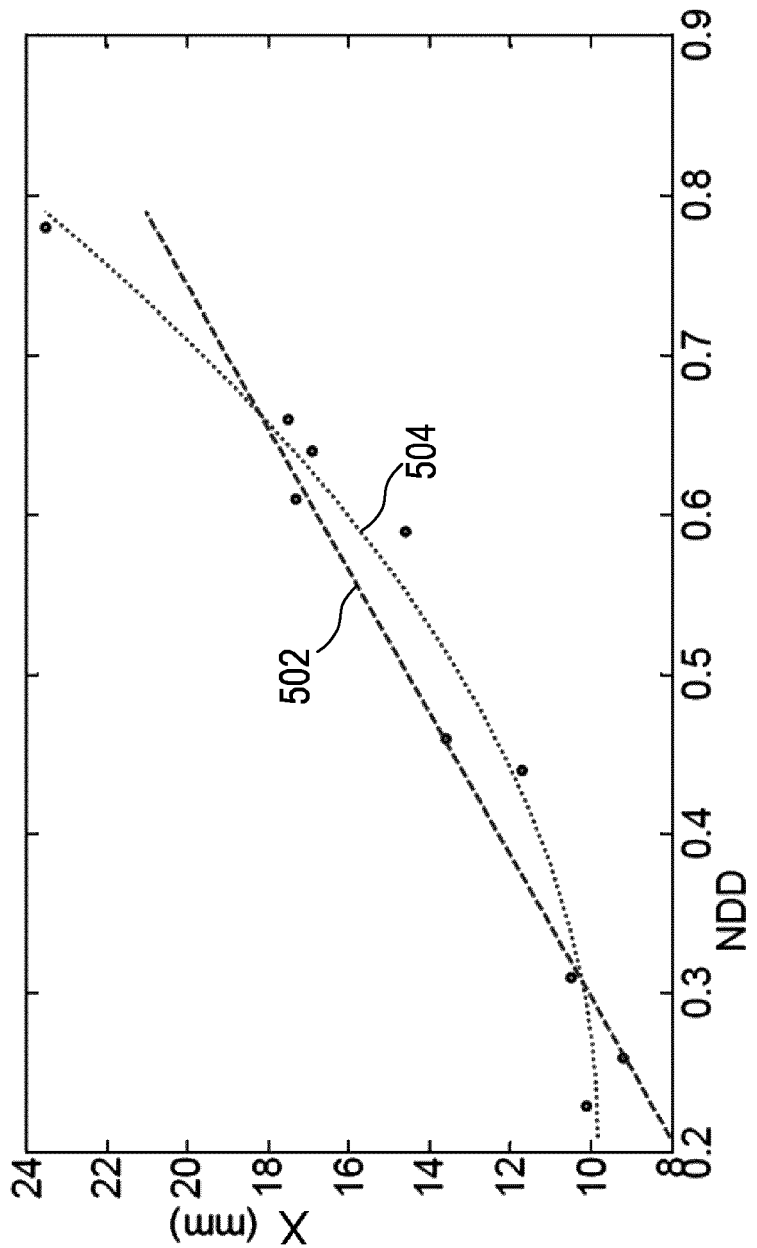
FIG. 5 is an exemplary illustration of a calibration of a tissue-monitoring device showing calibration points and two alternative calibration functions representing a dependence of a lesion diameter on a normalized displacement difference.

FIG. 5 summarizes the study and at the same time forms an exemplary illustration of the calibration of a tissue-monitoring device. Lesion size was measured by gross pathology. FIG. 5 shows the measurement results as calibration points and two alternative calibration functions, one linear and one quadratic representing alternative fits with different accuracy to the measurement point. The respective calibration function defines the extension x of the ablation zone (in other words, a lesion size) in mm with two calibration parameters as a linear function 502 of the normalized displacement difference NDD or with three calibration parameters as a quadratic function 504 of the normalized displacement difference NDD. As can be seen, there is a clear functional dependence of a lesion diameter on a normalized displacement difference NDD. The coefficients of determination (R squared) are 0.90 and 0.97 for linear and quadratic fitting, respectively. As FIG. 5 also shows, a coefficient of the quadratic term of this function is positive for the given example.

Figure 6:
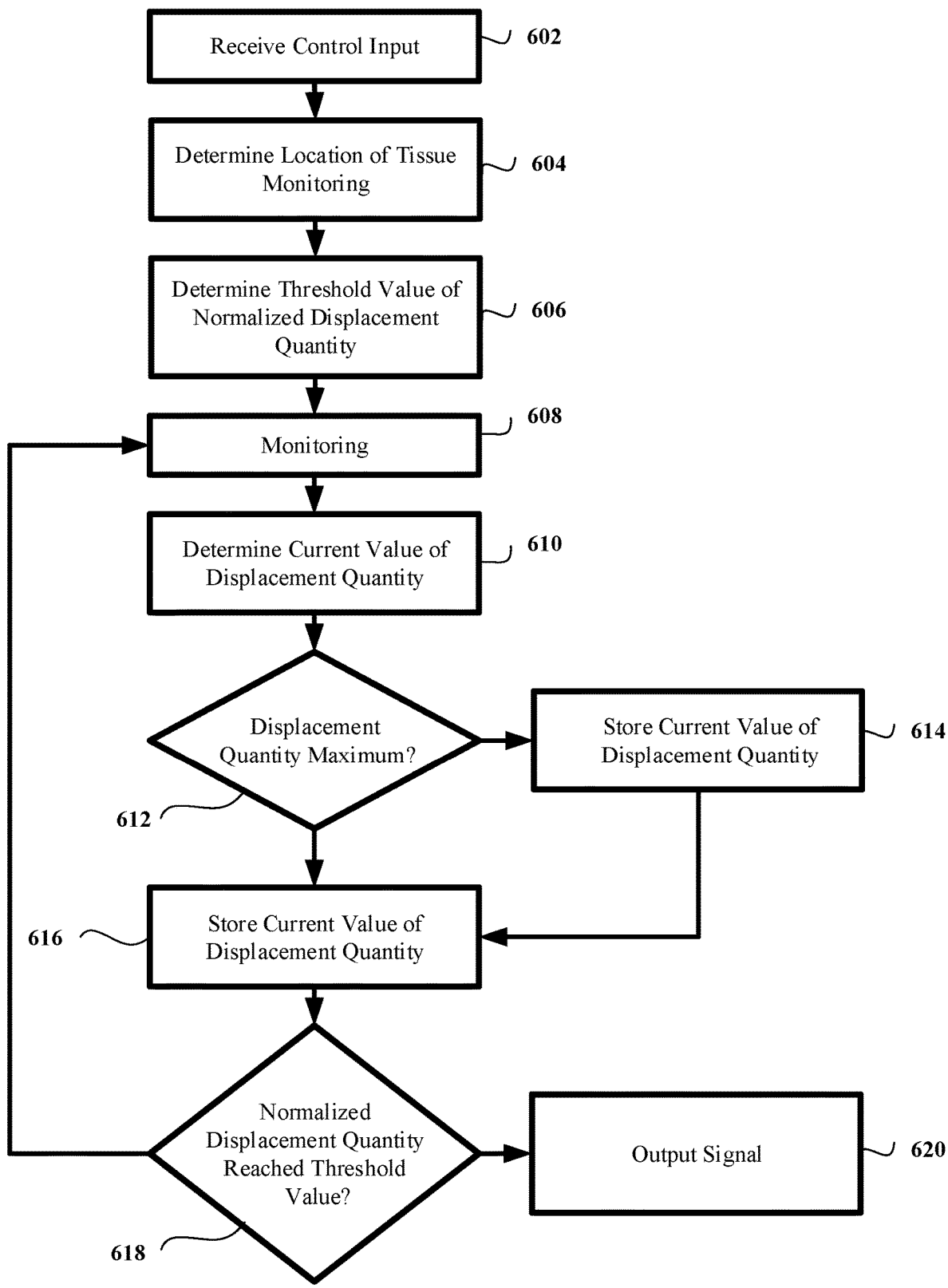
FIG. 6 shows a flow diagram of a method for monitoring biological tissue in a monitoring session during a delivery of energy to the tissue.

The results demonstrate the feasibility of monitoring RFA progress based on change in acoustic radiation force induced displacement in a plane on the periphery of the planned ablation zone. Different lesion sizes can be obtained using different NDD values. FIG. 6 shows a flow diagram of an embodiment of a tissue-monitoring method for monitoring biological tissue in a monitoring session during a delivery of energy to the tissue. The method is performed by a tissue-monitoring device, such as the tissue-monitoring device 110 of the embodiment of FIG. 1. The execution of the method may for instance be controlled by a computer, which is suitably implemented for example in the form of a programmable processor comprised by the tissue-monitoring device and executing a tissue-monitoring computer program controlling a performance of the method steps described in the following. Another embodiment uses only dedicated circuitry for implementing the tissue-monitoring device 110.

The tissue-monitoring method is started in a step 600. The start of the method is in one embodiment triggered by receiving a trigger signal from an energy-delivery device. The trigger signal indicates a concurrent start of an energy-delivery session to the biological tissue to be monitored. Another embodiment uses a manual triggering of the start of the tissue-monitoring method.

In a step 602, a control input is received. The control input is indicative of a desired spatial extension of a planned tissue ablation zone at a planned location of energy delivery. The control input can be provided in the form of a value indicative of an extension of the planned tissue ablation zone in one or more directions in space, and preferably provides the value with respect a known reference point. A suitable reference point is for instance a current position of an electrode of an energy-delivery probe inserted into the biological tissue. The reference point may correspond to a planned starting point of the ablation zone, or a planned center point, or any other point that allows a definition of the position and extension of the planned tissue ablation zone.

In a step 604 a location of tissue monitoring, herein also called monitoring location, is determined using the control input received in step 602. The monitoring location is in different embodiments determined in the form of a spot in the tissue, a one-dimensional tissue region (a tissue line), as a two-dimensional tissue region (a tissue plane) or as a three-dimensional tissue region (a tissue volume). A given tissue volume can for instance be monitored by monitoring different spots, lines or planes in the given tissue volume. The monitoring location is selected to be located at a peripheral location of the planned tissue ablation zone. Energy-delivery to biological tissue involves generation of heat at the planned ablation zone which is accompanied by formation of gas bubbles around a core of the ablation zone. This can introduce artefacts in displacement estimation at these locations, making tissue monitoring based on stiffness less reliable. Moreover, in minimally invasive therapy modalities, the therapy device applicator is present in the field of view of the ultrasound image. The presence of metal devices in soft tissue will disturb shear wave induction and propagation, and affect tissue displacement. Strong ultrasound backscatter reflections from the metal in these devices also introduce artefacts in displacement estimation. Based on these observations, the present embodiments avoid placing a monitoring location, for instance an ultrasound imaging plane, at or close to the core of the planned ablation zone. Rather, the monitoring location is selected planes on the periphery of the planned ablation zone. The periphery can be determined based on the position and extension of the planned ablation zone. In this case, the displacement change in these adjacent planes can be measured without perturbation until it is necrosed, assuming that the intervening region from the core of the lesion to this periphery is also ablated.

In a subsequent step 606, in dependence on the control input and on the determined monitoring location, a threshold value of a normalized displacement quantity is determined. The displacement quantity is indicative of an amount of tissue displacement detected. The normalized displacement quantity depends on a ratio between the value of the displacement quantity and a maximum of the displacement quantity observed during the monitoring session. This step is suitably performed by referring to an existing calibration, as described for instance with reference to FIG. 5 above. A preferred normalized displacement quantity used in the present context is the normalized displacement difference mentioned earlier. From the calibration, which provides an allocation of values of the extension of an ablation zone to values of the normalized displacement difference, a threshold value of the normalized displacement difference can be determined that will be reached, when the desired extension of the planned ablation zone has been achieved. This threshold value thus defines the end point of the energy-delivery. The threshold value can be described as $NDD_{th}(x) = 1 - ND_{end}(x)$ wherein
x is a quantity indicative of a desired spatial extension of a planned tissue ablation zone in the tissue,
$NDD_{th}(x)$ is the threshold value for a given desired spatial extension of the planned tissue ablation zone
$ND_{end}(x)$ is a value of the normalized displacement at the point of reaching the desired spatial extension x.

As FIG. 5 shows, the quantity NDD can be described in a first approximation as a linear function, or, with higher accuracy, by a quadratic function of the spatial extension of the planned ablation zone. The calibration is for instance stored in the form of pairs of values allocating NDD threshold values to an input spatial extension of the planned ablation zone. The calibration is in another variant provided in the form calibration parameters of a predetermined linear or quadratic function, and the NDD threshold value to be used in a monitoring session for a given input spatial extension of the planned ablation zone is determined by calculation using the calibration function.

Subsequently, the monitoring is performed from step 608 on by repeatedly driving a single measurement probe in providing at least one ultrasonic push pulse that is suitable for displacing the tissue at a monitoring location, and in providing ultrasonic track pulses suitable for detecting tissue displacement occurring in response to the push pulse at the monitoring location, and in detecting ultrasonic tissue-response signals in response to the track pulses. These steps have been described in more detail with reference to FIG. 3 and are summarized in one step 608 here in the flow diagram of FIG. 6. The rate of repetition of this measurement is in one embodiment controllable by user input. In another embodiment, it is determined automatically, for instance in dependence on control input parameters such as the extension of the planned tissue ablation zone.

The method further comprises determining from the tissue-response signals in real time the following:
a current value of the displacement quantity (step 610) is determined, in particular, the tissue displacement D(t), which is indicative of an amount of tissue displacement detected in response to the push pulse.
it is determined whether the determined value of the displacement quantity forms a maximum of the displacement quantity with respect to the values determined so far during the monitoring session (step 612). In determining the maximum, a smoothing algorithm may be applied to the incoming values of the displacement quantity. If a maximum is currently detected, the current value of the displacement quantity D(t) is stored as the current maximum $D_{max}$ (step 614). If the current value of D(t) does not form a maximum, a previously stored maximum is used in step 616 for calculating the normalized displacement quantity $$ND(t) = \frac{D(t)}{D_{max}}.$$

As a next step (step 616), the normalized displacement difference is determined as $NDD(t) = 1 - ND(t).$ Furthermore, in step 618 it is determined whether the normalized displacement quantity has reached the threshold value $NDD_{th}(x)$. If that is the case, an output signal is provided (step 620). The output signal is used by an external energy-delivery device to stop the energy delivery to the ablation zone. If that is not the case, the method branches back to step 608 and performs a next measurement and evaluation cycle, after a predetermined waiting time.

The waiting time is typically in the range between 5 and 20 seconds. The waiting time is selected in dependence on several factors. One is lesion size. For smaller lesion sizes, the waiting time is preferably smaller than for lager lesion sizes. Another factor is a power density, for instance in terms of power per cubic centimetre, used for energy delivery. A higher power density requires a higher monitoring frequency than a lower power density. The waiting time may also depend on the tissue type. Different tissue types have different heat capacities and different sensitivities to energy exposure, and therefore may require different monitoring frequencies.

Typically, an energy-delivery session, such as an ablation treatment, extends over a time span of a few minutes, such as for instance 15 to 20 minutes. An exemplary suitable repetition rate for monitoring an energy-delivery session of this time span is in the range between 5-20 seconds for most applications. This value depends on time constants for a thermal heat diffusion process in the tissue. It also depends on acoustic output and transducer cooling requirements of the equipment used.

In a clinical implementation, based on a therapy planning output, which typically precedes monitoring, a clinician can "dial" in the desired lesion size to treat the tumor. Based on a calibration curve obtained as prescribed in this invention, the tissue-monitoring device then calculates a threshold NDD value forming a target value corresponding to this lesion size. During therapy, the NDD is calculated in real-time and compared with the target value. When the target value is reached, the therapy delivery stops and the treatment end point has been attained.

Thus, the tissue monitoring according to embodiments of the present invention comprises assessing the normalized displacement difference relative to the peak displacement as a particularly suitable quantity indicative of a mechanical stiffening of tissue in a periphery of a tissue ablation zone in real-time during energy-delivery to effect tissue ablation, and predicting when the desired volume is necrosed. Tissue stiffness is obtained by measuring tissue displacement in response to acoustic radiation force in an ultrasound monitoring location, such as an imaging plane on the periphery of the planned ablation zone. A size or an extension of the tissue ablation zone can be predicted based on the normalized displacement difference relative to the peak displacement at the end point of treatment. That is, by stopping ablation at different normalized displacement levels, different lesion sizes will be obtained in a predictable way.

In summary, the present invention relates to monitoring biological tissue during a delivery of energy. A probe-driving unit repeatedly drives an integrated push-and-track transducer unit, which is external to the control device, in repeatedly providing at least one ultrasonic push pulse that is suitable for displacing biological tissue at a monitoring location, and in providing ultrasonic track pulses suitable for detecting tissue displacement occurring in response to the push pulse at the monitoring location, and in detecting and delivering ultrasonic tissue-response signals relating to the track pulses. An evaluation unit receives the tissue-response signals, determines in real time whether a normalized displacement quantity has reached a threshold value, and provides an output signal when the threshold value has been reached.

The present invention can be used for providing medical treatment. One advantageous application of the present invention is a method of medical treatment by delivering energy to tissue of a living body, comprising
- delivering energy in an energy amount suitable for necrosing tissue to a desired ablation zone of the tissue via an energy-delivery probe positioned at a delivery location,
- performing a monitoring session for monitoring the tissue according to the method of the third aspect of the present invention or one of its embodiments, and
- ending the treatment when the output signal has been provided.

The method may for instance be used for tumor ablation. However, it is not limited to tumor ablation. An alleviation of cardiac arrhythmia, for example, may be accomplished by necrosing a specific line of heart tissue to thereby block an abnormal electrical path through the heart. Such a method may be accomplished using monitored energy delivery methods of the present invention.

Moreover, although methodology of the present invention can advantageously be applied in providing medical treatment, the scope of the present invention is not so limited. Techniques of the present invention are directed to delivering energy to cause a mechanical property of biological tissue in vivo, in vitro or ex vivo to change and to examining, in at least one spatial dimension, an effect of the energy delivery.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit may fulfill the functions of several items recited in the claims.

The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A tissue-monitoring device for monitoring biological tissue in a monitoring session during a delivery of energy to the biological tissue, comprising:
   a memory that stores instructions, and
   a processor that executes the instructions, wherein, when executed by the processor, the instructions cause the tissue-monitoring device to implement a process comprising:
   providing probe-driving signals suitable for driving an integrated push-and-track transducer of a measurement probe, which is external to the tissue-monitoring device, to repeatedly provide at least one ultrasonic push pulse that is suitable for displacing biological tissue at a monitoring location, to provide ultrasonic track pulses suitable for detecting tissue displacement occurring in response to the ultrasonic push pulse at the monitoring location, and to detect and deliver ultrasonic tissue-response signals relating to the ultrasonic track pulses;

repeatedly determining in real time during the monitoring session based on the ultrasonic tissue-response signals: a current value of a displacement quantity indicative of an amount of tissue displacement detected, a current maximum of the displacement quantity since a beginning of the monitoring session, a ratio between the current value and the current maximum of the displacement quantity, a normalized displacement quantity that uses the ratio between the current value and the current maximum of the displacement quantity, and whether the normalized displacement quantity has reached a threshold value; and providing an output signal when the threshold value has been reached.

2. The tissue-monitoring device of claim 1, wherein, when executed by the processor, the instructions further cause the tissue-monitoring device to:

receive a control input indicative of a desired spatial extension of a planned tissue ablation zone at a planned location of energy delivery, determine, from the control input, the monitoring location at a peripheral location (P) of the planned tissue ablation zone, and determine the threshold value of the normalized displacement quantity in dependence on the determined monitoring location.

3. The tissue-monitoring device of claim 1, wherein, when executed by the processor, the instructions further cause the tissue-monitoring device:

to determine the normalized displacement quantity as a normalized displacement difference according to $$NDD(t)=1-ND(t),$$

wherein $$ND(t) = \frac{D(t)}{D_{max}(t)},$$

t is a time difference with respect to a beginning of the monitoring session,

ND(t) is the current value of the normalized displacement,

D(t) is the current value of the displacement quantity, $D_{max}(t)$ is the current maximum of the displacement quantity detected during the monitoring session, and NDD(t) is the normalized displacement difference, and to determine from the determined normalized displacement difference an extension of a planned tissue ablation zone using a calibration function with prestored calibration parameters.

4. The tissue-monitoring device of claim 3, wherein the calibration function defines the extension of the planned tissue ablation zone with two calibration parameters as a linear function of the normalized displacement difference or with three calibration parameters as a quadratic function of the normalized displacement difference.

5. The tissue-monitoring device of claim 4, wherein, when executed by the processor, the instructions further cause the tissue-monitoring device to receive a desired spatial extension of a planned tissue ablation zone in the biological tissue, and to determine, using the calibration function, a threshold value of the normalized displacement difference for a given desired spatial extension of the planned tissue ablation zone.

6. The tissue monitoring device of claim 1, wherein, when executed by the processor, the instructions further cause the tissue-monitoring device to drive the push-and-track transducer in providing a first ultrasonic track pulse before providing the ultrasonic push pulse and a second ultrasonic track pulse after providing the ultrasonic push pulse.

7. A tissue-monitoring system, comprising:

a tissue monitoring device of claim 1; and a measurement probe, which is configured to receive the probe-driving signals and to deliver the ultrasonic tissue-response signal and which comprises an integrated push-and-track transducer configured to provide the at least one ultrasonic push pulse and the ultrasonic track pulses, and which is configured to detect the ultrasonic tissue-response signals relating to the ultrasonic track pulses.

8. An energy-delivery system for delivering energy to biological tissue, comprising:

an energy-delivery probe, which is configured to deliver energy in an energy amount suitable for necrosing tissue to a desired ablation zone of the tissue when positioned at a delivery location; and a tissue-monitoring system according to claim 7;

wherein the energy-delivery system is configured to receive the output signal provided by the tissue-monitoring device and to stop delivering energy upon reception of the output signal.

9. The tissue-monitoring device of claim 7, wherein the measurement probe comprises a single integrated-push-and-track transducer for the delivery of both, the at least one ultrasonic push pulse and the ultrasonic track pulses, and which is configured to detect and deliver the ultrasonic tissue-response signals.

10. An energy-delivery system for delivering energy to biological tissue, comprising:

an energy-delivery probe, which is configured to deliver energy in an energy amount suitable for necrosing tissue to a desired ablation zone of the tissue when positioned at a delivery location; and a tissue-monitoring device according to claim 1;

wherein the energy-delivery system is configured to receive the output signal provided by the tissue-monitoring device and to stop delivering energy upon reception of the output signal.

11. The tissue monitoring device of claim 1, wherein the current maximum of the displacement quantity is increased from a first current maximum of the displacement quantity to a second current maximum of the displacement quantity during the monitoring session based on detecting a current value of the displacement quantity equal to the second current maximum of the displacement quantity and greater than the first current maximum of the displacement quantity.

12. A monitoring method for monitoring biological tissue in a monitoring session during a delivery of energy to the biological tissue, comprising:

providing, from a tissue-monitoring device, probe-driving signals suitable for driving an integrated push-and-track transducer of a measurement probe, which is external to the tissue-monitoring device, in repeatedly providing at least one ultrasonic push pulse that is suitable for displacing biological tissue at a monitoring location, and in providing ultrasonic track pulses suitable for detecting tissue displacement occurring in response to the ultrasonic push pulse at the monitoring location, and suitable for detecting and delivering ultrasonic tissue-response signals relating to the ultrasonic track pulses;

repeatedly determining from the ultrasonic tissue-response signals in real time and based on the ultrasonic tissue-response signals: a current value of a displacement quantity, which is indicative of an amount of tissue displacement detected; a current maximum of the displacement quantity since a beginning of the monitoring session; a ratio between the value of the displacement quantity and the current maximum of the displacement quantity; a current value of a normalized displacement quantity, which uses the ratio between the value of the displacement quantity and the current maximum of the displacement quantity, and whether the normalized displacement quantity has reached a predetermined threshold value of the normalized displacement quantity; and providing an output signal when the predetermined threshold value of the normalized displacement quantity has been reached.

13. The method of claim 12, further comprising:

receiving a control input indicative of a desired spatial extension of a planned tissue ablation zone at a planned location of energy delivery;

determining, from the control input, a monitoring location at a peripheral location of the planned tissue ablation zone; and determining, in dependence on the determined monitoring location, the threshold value of the normalized displacement quantity.

14. The method of claim 12, further comprising, determining the normalized displacement quantity as a normalized displacement difference according to $NDD(t) = 1 - ND(t)$, wherein $$ND(t) = \frac{D(t)}{D_{max}}$$

t is a time difference with respect to a beginning of the monitoring session $ND(t)$ is the current value of the normalized displacement, $D(t)$ is the current value of the displacement quantity, $D_{max}$ is the current maximum of the displacement quantity detected during the monitoring session, and $NDD(t)$ is the normalized displacement difference; and determining from the determined normalized displacement difference an extension of a planned tissue ablation zone using a calibration function with prestored calibration parameters.

15. A method for delivering energy to biological tissue, comprising delivering energy in an energy amount suitable for necrosing tissue to a desired ablation zone of the tissue via an energy-delivery probe positioned at a delivery location;

performing a monitoring session for monitoring the tissue according to the method of claim 10, and ending the delivery of energy when the output signal has been provided.

16. The method of claim 12, wherein the method is implemented when a computer executes a tissue-monitoring control computer program to cause the computer to carry out the method when the computer program is executed on the computer.

17. The method of claim 15, wherein the method is implemented when a computer executes an energy-delivery control program to cause the computer to carry out the method when the computer program is executed on a computer.

18. The method of claim 12, wherein the current maximum of the displacement quantity is increased from a first current maximum of the displacement quantity to a second current maximum of the displacement quantity during the monitoring session based on detecting a current value of the displacement quantity equal to the second current maximum of the displacement quantity and greater than the first current maximum of the displacement quantity.

19. The method of claim 18, further comprising:

determining the normalized displacement quantity based on the second current maximum of the displacement quantity; and determining whether the normalized displacement quantity has reached the predetermined threshold value of the normalized displacement quantity after determining the normalized displacement quantity based on the second current maximum of the displacement quantity.

\* \* \* \* \*